(12) United States Patent
Vyavahare et al.

(10) Patent No.: US 6,837,903 B2
(45) Date of Patent: Jan. 4, 2005

(54) VASCULAR BIOMATERIAL DEVICES AND METHODS

(75) Inventors: Naren R. Vyavahare, Easley, SC (US); John J. Marigliano, Central, SC (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 10/105,071

(22) Filed: Mar. 22, 2002

(65) Prior Publication Data

US 2003/0181976 A1 Sep. 25, 2003

(51) Int. Cl.⁷ .................................................. A61F 2/06
(52) U.S. Cl. ...................... 623/2.42; 623/1.46; 427/2.25
(58) Field of Search ................... 623/2.42, 1.46, 623/1.25; 600/36; 427/2.1, 2.24, 2.25

(56) References Cited

U.S. PATENT DOCUMENTS

| | | | |
|---|---|---|---|
| 4,806,382 A | | 2/1989 | Goldberg et al. |
| 4,961,954 A | | 10/1990 | Goldberg et al. |
| 5,080,893 A | | 1/1992 | Goldberg et al. |
| 5,100,689 A | | 3/1992 | Goldberg et al. |
| 5,108,776 A | | 4/1992 | Goldberg et al. |
| 5,130,160 A | | 7/1992 | Goldberg et al. |
| 5,290,548 A | | 3/1994 | Goldberg et al. |
| 5,376,400 A | | 12/1994 | Goldberg et al. |
| 5,387,247 A | * | 2/1995 | Vallana et al. ............. 623/2.42 |
| 5,439,736 A | * | 8/1995 | Nomura ................... 428/308.4 |
| 5,496,277 A | | 3/1996 | Termin et al. |
| 5,500,014 A | | 3/1996 | Quijano et al. |
| 5,713,950 A | | 2/1998 | Cox |
| 5,766,240 A | | 6/1998 | Johnson |
| 5,811,151 A | * | 9/1998 | Hendriks et al. .......... 427/2.24 |
| 5,919,226 A | * | 7/1999 | Shu et al. .................. 623/2.31 |
| 6,093,530 A | | 7/2000 | McIlroy et al. |
| 6,344,496 B1 | | 2/2002 | Niederauer et al. |
| 6,372,283 B1 | * | 4/2002 | Shim et al. ................ 427/2.25 |
| 6,387,379 B1 | * | 5/2002 | Goldberg et al. ........... 424/400 |

OTHER PUBLICATIONS

"Bileaflet Disc Heart Valves", pp. 1–6,. http://www.csm-c.edu/cvs/md/valve/disk2.htm.
Article—*Role of endothelial cell–substrate contact area and fibronectin–receptor affinity in cell adhesion to HEMA/EMA copolymers*, Jeffrey S. Burmeister, Valerie Z. McKinney, William M. Reichert, and George A. Truskey, J. Biomed. Mater. Res., vol. 47, 1999, pp. 577–584.
Article—*Plasma deposition for biomedical applications: A brief review*, Buddy D. Ratner, J. Biomater. Sci. Polymer Edn., vol. 4, No. 1, 1992, pp. 3–11.

* cited by examiner

*Primary Examiner*—Corrine McDermott
*Assistant Examiner*—Kamrin R. Landrem
(74) *Attorney, Agent, or Firm*—Dority & Manning, P.A.

(57) ABSTRACT

Vascular biomaterial structures may be coated with a plasma-induced layer on their surface. Vascular biomaterial structures may include cardiovascular devices such as heart valves, stents, vascular graphs, and the like. Devices coated with a plasma polymerized coating may show reduced amounts of undesirable coagulation of blood at the surface of the device. A reduced amount of thrombosis may be observed for such plasma coated medical devices.

33 Claims, 3 Drawing Sheets

VASCULAR BIOMATERIAL DEVICES AND METHODS

FIELD OF THE INVENTION

The invention is directed to vascular biomaterials which include a plasma-induced coating upon their surface. In particular, the invention may be directed to apparatus and methods for increasing biological compatibility of synthetic cardiovascular biomaterial by application of a plasma coating process.

BACKGROUND OF THE INVENTION

Thrombosis is a primary method of failure for artificial or mechanical cardiovascular biomaterials, such as heart valves. Thrombosis refers to the undesirable coagulation of blood at or near the surface of such a structure. Current mechanical heart valves have demonstrated improved mechanical properties and durability. However, the constant contact of mechanical heart valves with blood sometimes leads to the formation of blood clots following undesirable thrombosis. Thus, thrombosis and blood clotting is a major concern in mechanical biomaterial design, including particularly heart valve design.

To prevent thrombosis, it is common to place patients upon long-term anticoagulation therapy. However, such therapy is expensive, and may pose other risks or side effects. Thus, anticoagulation therapy is not an ideal solution.

Every year, it is estimated that over 150,000 heart valve replacement surgeries are performed, with more than half occurring in the United States alone. When a natural heart valve becomes diseased and is no longer able to function properly, valve replacement therapy may be necessary. The most commonly replaced valves are the aortic and mitral. Success rates for valve replacement surgeries have risen, and surgeons currently are likely to employ replacement as a treatment for damaged natural valves.

What is needed in the industry and in the medical community is an improved biomaterial that is less prone to undesirable thrombosis. Also, a method of constructing a suitable biomaterial which lessens the incidence of undesirable blood clotting would be very desirable. In particular, a mechanical heart valve that reduces the incidence of thrombosis when surgically implanted is needed.

SUMMARY OF THE INVENTION

In one aspect of the invention, a vascular biomaterial is provided comprising a metallic support structure and a plasma polymerized coating which is adhered to the support structure. In some applications, the vascular biomaterial comprises a valve. In other applications, the vascular biomaterial may include a stent, a vascular graft, or another structure adapted for implantation, which could be in contact with blood tissue.

The support structure in one aspect of the invention may include carbon, such as pyrolytic carbon. In other aspects of the invention, it may be possible to provide a method of coating a vascular biomaterial using plasma deposition techniques. In the method, a monomer is polymerized upon a reactive surface of the support structure using plasma deposition techniques. The monomer may contain a hydroxyl, carboxyl, sulfonate, or amine group. The monomer may contain a methacrylate-containing species or a styrene-containing species. In these embodiments, the plasma polymerized coating adhered to the support structure can comprise a polymerized monomer of a methacrylate-containing species or a polymerized monomer of a styrene-containing species.

BRIEF DESCRIPTION OF THE DRAWINGS

A full and enabling disclosure of this invention, including the best mode shown to one of ordinary skill in the art, is set forth in this specification. The following Figures illustrate the invention.

DETAILED DESCRIPTION OF THE INVENTION

Figure 1:
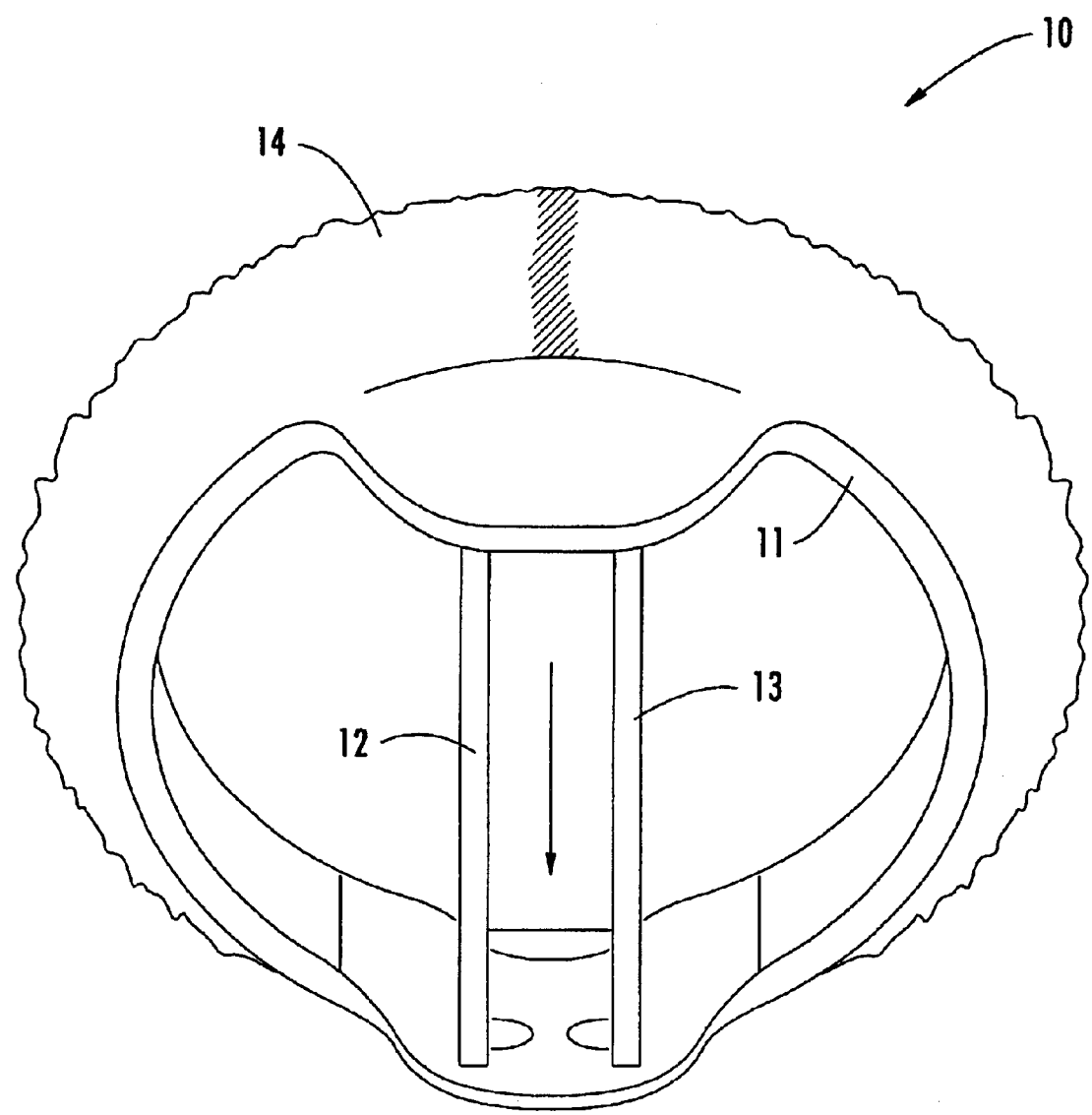
FIG. 1 is a perspective view of a typical bileaflet mechanical heart valve.

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention.

When a heart valve must be replaced with a prosthetic valve, there currently are several options available. The choice of a particular type of prosthesis (i.e., artificial valve) depends on factors such as the location of the valve, the age and other specifics of the patient, and the surgeon's experiences and preferences. Available prostheses include three categories of valves or materials: mechanical valves, tissue valves, and aortic homograft valves.

Mechanical valves include caged ball valves (such as Starr-Edwards brand valves), bileaflet valves (such as St. Jude type valves), and tilting disk valves (such as Medtronic-Hall or Omniscience valves). Caged ball valves usually are made with a ball made of a silicone rubber inside a titanium cage, while bileaflet and tilting disk valves are made of various combinations of pyrolytic carbon and titanium. All of these valves are attached to a cloth sewing ring so that the valve prosthesis may be sutured to the patient's native tissue to hold the artificial valve in place postoperatively. All of these mechanical valves can be used to replace any of the four heart valves. Valve function may be related to platelet activation, as further discussed below.

Blood platelets are non-nucleated, disc shaped cells with a diameter of approximately 3–4 $\mu$m. The basic function of platelets is to assist in the clotting of blood by forming platelet plugs and catalyzing coagulation reactions leading to the formation of fibrin networks. Platelets are very sensitive cells, and upon activation, their shape becomes more irregular and spread out as the contents of their granules are released into the extracellular matrix. The release of these platelet products stimulates surrounding platelets, causing irreversible platelet aggregation leading to a thrombus formation.

It has been shown that flow dynamics play an important role in the localization of platelet aggregation on bileaflet mechanical heart valves, initiating thrombus formations. Localized jets, steep velocity gradients, and vortex recirculation have been observed in vitro near leaflet surfaces. In vivo flow patterns promote recirculation of blood toward the pivot points, and leakage through gaps created at the pivot-leaflet junction is believed to be a major factor responsible for platelet damage. As a result, it has been demonstrated that platelet aggregation is concentrated at the leaflet edges and pivot points.

Modern implantable prosthetic mechanical heart valves are typically formed of an annular valve seat in a relatively rigid valve body and one or more occluding spheres, disks or leaflets that are movable between a closed, seated position in the annular valve seat and an open position in a prescribed range of motion. Such mechanical heart valves may be formed of blood compatible, non-thrombogenic materials. Pyrolytic carbon and titanium may be used, with hinge mechanisms or pivoting guides prescribing the range of motion of the disk or leaflets.

Typical rotatable suturing rings for asymmetric mechanical valves are shown in U.S. Pat. Nos. 3,727,240, 3,763,548, 3,781,969, 3,800,403, 3,835,475, 4,197,593, 5,766,240 and U.S. Re. Pat. No. 30,507; and are incorporated by reference. Prosthetic vascular grafts are also known. Examples of vascular prostheses are described in U.S. Pat. No. 5,500,014. Furthermore, grafts or blood vessels prepared from artificial materials are disclosed in U.S. Pat. No. 4,086,665, issued to Poirier on May 2, 1978; U.S. Pat. No. 4,118,806, issued to Poirier on Oct. 10, 1978; and U.S. Pat. No. 4,670,286, issued to Nyilas et al on Jun. 2, 1987.

The invention of this application could employ plasma induced surface modification techniques upon vascular grafting materials. Vascular grafts may be prepared from synthetic structures. Grafts are prepared by chemically treating segments of biografts. Examples of these various grafts are disclosed in U.S. Pat. No. 4,671,797, issued to Vrandecic Pedero on Jun. 9, 1987 and U.S. Pat. No. 4,466,139, issued to Ketharanathan on Aug. 21, 1984. The invention may be directed to providing a plasma polymerized coating upon a synthetic graft support structure. The invention may include grafting olefinic monomers or polymers upon a metallic support structure of a mechanical heart valve.

The invention of this application could be applied to stents as well. Stents are disclosed in U.S. Pat. No. 5,496,277. Furthermore, U.S. Pat. No. 4,699,611 (Bowden) is directed to stents which hold arteries, veins, and the like in an open position when inserted.

Mechanical heart valves made from pyrolytic carbon (PyC) may be used to replace diseased or damaged native valves, as they offer good durability and mechanical strength. Furthermore, other composite or metallic materials could be employed as a support material or support structure in the invention.

Bileaflet Valves

A very successful bileaflet valve employed in the medical community is the St. Jude valve. FIG. 1, as further discussed below, shows the St. Jude valve. In general, the widespread acceptance and relatively large market share of the St. Jude valve has led to a host of competing bileaflet valve designs. Many of these alternative designs represent relatively minor variations on the hinged system of the St. Jude valve. Clearly, the invention could be applied to any artificial biomaterial structure, including for example any artificial valve, as further described herein. Thus, the types of valve described herein are shown as mere examples of the application of the invention, and are not limiting in any way.

Some of the other valves which could be employed in the practice of the invention include the ATS bileaflet valve, manufactured by ATS, Inc. Furthermore, the Carbomedics valve is a bileaflet tilting disk valve made of pyrolytic carbon. The Carbomedics valve is actively implanted in the United States. The Carbomedics valve is manufactured by Sulzer Carbomedics, Inc. of 1300 East Anderson Lane, Austin, Tex. 78752. Another valve that may be employed is the Edwards Duromedics valve. The Edwards Duromedics valve is a bileaflet valve which may be provided for mitral or aortic concave bileaflet designs. The manufacturer was originally Hemex Scientific, but later was manufactured by Baxter-Edwards, Inc.

Another valve that may be employed in the practice of the invention is the Medtronic Parallel Valve. The Medtronic Parallel Valve is a bileaflet valve with a pivot mechanism. The pivot allows the leaflets to open to fully parallel, in contrast to the opening of the St. Jude valve leaflets which is only about 85 degrees in most applications. The Medtronic Parallel Valve is manufactured by Medtronic, Inc.

Another pyrolytic carbon bileaflet valve which may be employed in the practice of the invention is On-X valve. The On-X valve is manufactured by Medical Carbon Research Institute, LLC at 8200 Cameron Road, Suite A-196, Austin, Tex. 78754.

The St. Jude valve, as previously discussed, is particularly adapted for the practice of this invention because it provides excellent durability, good hemodynamics, and is very common in the United States mechanical valve market. The St. Jude valve is manufactured by St. Jude Medical, Inc., 1 Lillehei Plaza, St. Paul, Minn. 55117. In at least one model, the St. Jude valve comprises support structure of pyrolytic carbon, with a sewing ring of double velour knitted polyester. Furthermore, a master series is available with an attached helical spring and two retainer rings which are rotatable. The St. Jude valve is available in sizes as follows: aortic—19 mm, 25 mm; mitral—25 mm, 33 mm, and perhaps others as well.

Turning to FIG. 1, a St. Jude bileaflet valve 10 is shown having a valve body 11 or support structure which supports a first leaflet 12 and a second leaflet 13. The first leaflet 12 and the second leaflet 13 are oriented generally parallel to each other across the diameter of the support structure or valve body 11. The first and second leaflets 12–13 are hingedly connected to the valve body 11 so that upon application of force they hinge open to allow maximum blood flow through the valve. In FIG. 1, the bileaflet valve is shown with the first and second leaflets 12–13 in the open position. Furthermore, a suturing ring 14 is shown around the periphery of the support structure. The suturing ring 14 is used to stitch the valve in place during surgical operations.

One application of the invention provides a nonthrombogenic surface coating for mechanical heart valves by generating a plasma induced polymeric surface treatment. To achieve this goal, it is possible to use almost any known polymer that is capable of polymerizing in a plasma reaction chamber to form a surface coating upon a support structure.

For example, one particular embodiment of the invention employs two monomers, 2-hydroxyethyl methacrylate (HEMA) and acrylic acid, of different functionalities, to form coatings upon such surfaces.

Such coatings may be applied to the St. Jude valve, which combines the hemodynamic advancements, a tilting disc design with the enhanced biocompatibility and durability of pyrolytic carbon ("PyC"). With the exception of the suture ring 14, which is made of polyester, the entire St. Jude valve is composed of graphite coated with PyC, prior to receiving a plasma induced outer coating according to the practice of this invention.

Pyrolytic Carbon

Pyrolytic carbon (PyC) refers to the collection of solid, carbon rich species from the heating of organic gases to temperatures exceeding 1000° C. at which point the hydrocarbon decomposes into elemental carbon, which is then deposited onto a substrate. By manipulating certain variables during this process, multiple structures of PyC can be manufactured with wide ranging applications.

The mechanical properties of PyC completely depend upon the structure. In comparison to the more familiar structure of graphite, in which the layers are ordered with respect to one another so that the crystal structure is three-dimensional, PyC possesses two-dimensional order. The layers consist of hexagonal planes of carbon, which are primarily held together by strong covalent bonds and van der Waals interactions. However it has been shown that in its strongest form, PyC contains cross-links that form between planes.

PyC formed at relatively low temperatures (1000–1500° C.), is isotropic, and highly cross-linked. As a result of the high degree of cross-linking between planes, so called Low Temperature Isotropic Pyrolytic Carbon is the strongest and hardest type of PyC with a scratch hardness near that of diamond. It has been shown that PyC deposited at higher temperatures (1900° C. and above) have larger grains visible in their microstructures, and cracks which form in these grains under stress, can ultimately lead to fracture. High temperatures large growth features develop and may act as stress raisers causing failure under low loads.

The type of reactor plays an important role in determining the structure of PyC. For example, a simple static reactor produces a highly oriented, anisotropic PyC, which is used in rocket nozzles, but not suitable for mechanical heart valves. In order to produce the pyrolytic carbon used in mechanical heart valves, a fluidized bed reactor is necessary. A fluidized bed consists of a large number of small particles, which behave as a liquid when suspended in an upward flowing gas.

Plasma Coating Processes

Often referred to as the fourth state of matter, plasma is simply a gas containing a mixture of electrons, ions, radicals, and neutral species. Plasmas can be generated through electron excitation as a result of the application of radio frequency, microwave, or heat energy. Under the right conditions, plasmas can be used to deposit molecules onto surfaces. Plasma may provide a thin coating without altering the bulk properties of the base support material.

The energy used to initiate the plasma causes the electrons to oscillate, which can heat the electrons sufficiently enough to provide the required ionization. This process is known as breakdown. Following breakdown, the next state is called glow discharge, as light is emitted from the plasma. Most of the energy used in this system is to accelerate electrons and ions through the sheath, the area between the plasma and the substrate (See FIG. 3). The energy from ion and electron bombardment is enough to break chemical bonds on the surface of the substrate, and it is this property of plasma deposition that promotes the creation of highly reactive species. By varying the plasma gases, it is possible to obtain a wide variety of functional groups deposited on the surface of a support structure of a biomaterial.

One advantage of plasma technology in applying coatings to biomaterials such as heart valves is the ability to produce ultra thin polymer surfaces. Plasma polymerization results in highly cross-linked polymeric surfaces that strongly adhere to the underlying substrate. The underlying substrate is pyrolytic carbon in the case of the St. Jude heart valve. These reactions are very complex and highly system dependent, thus they are governed by many parameters such as the monomer gas used, substrate properties, reaction conditions (power, pressure, flow rate, reaction time), the placement and orientation of the sample within the reaction chamber, and the type of reaction chamber used. Through the variation of these parameters, it is possible to create a wide variety of polymers from a single monomer.

There are at least two methods in which to plasma polymerize a given surface of a biomaterial support structure. One method is to simply allow a monomer vapor into the reaction chamber and initiate a plasma. This would then lead to the creation and deposition of monomer radicals, which upon reacting with each other, results in a thin polymer layer.

A second method is to initially create a reactive surface with a non-reactive gas plasma such as oxygen or argon, and then expose this reactive surface to a monomer solution. When a surface is first treated with an oxygen plasma and then exposed to the air, reactive peroxides are generated on the surface, which initiate the polymerization reaction when the material is exposed to the monomer solution. This form of surface modification is known as plasma induced polymerization, in which plasma deposition is initially used to generated a reactive surface that will induce polymerization. Traditionally, planer reactors, which accelerate ions in one direction between charged plates, have been used for plasma deposition, however barrel reactors offer the advantage of deposition without the possibility of etching the substrate.

Figure 2:
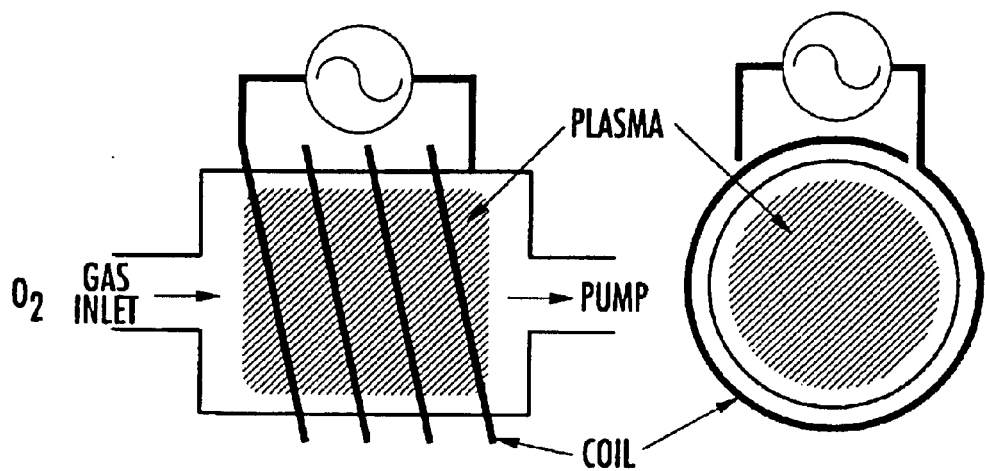
FIG. 2 shows a diagram of a typical barrel reactor that may be used to provide a plasma coating.

A barrel reactor, shown in FIG. 2, inductively couples AC power through coils that surround the reaction chamber. This allows for a smaller sheath, which prevents electron and ionic bombardment that may lead to etching.

The advantages of plasma polymerization are numerous but are best demonstrated in comparison to conventional surface polymerization. In order to create a polymer coating using conventional processes the following steps would have to be taken: synthesis of the polymer, preparation of the coating solution, process the coating, dry and cure the final product. In plasma polymerization, these steps may be combined, and polymerization usually occurs directly from the monomer. Many coatings are simply not capable of being achieved by conventional means.

The processing of the polymeric coatings of the invention employs an oxygen plasma to create a reactive surface upon the support structure of the vascular biomaterial that can induce polymerization when in contact with the liquid monomer solution.

The surface modification was assessed by water droplet contact angle determination, which shows extent of surface hydrophilicity and electron spectroscopy for chemical processes. Both contact angle and ESCA (Electron Spectroscopy for Chemical Analysis) indicated significant changes in the surface characteristics of modified PyC and polystyrene as a result of such polymeric coatings. In both cases, hydrophobic materials were altered to produce highly hydrophilic surfaces with significantly increased surface oxygen content. Polymerized samples demonstrated increases in both carbonyl and hydroxyl groups. Surface hydrophilicity and oxygen content are both accepted factors for enhanced biocompatibility and endothelial cell growth.

The results of surface modification demonstrate an increase in the growth of endothelial cells on both PyC and untreated polystyrene substrates, as these surfaces were able to produce confluent cell layers in a shorter time period. Untreated polystyrene samples do not generally promote favorable cell growth, and the increase in endothelialization can most likely be attributed to the presence of oxygen containing functional groups generated by our polymeric coating. The increase of cell growth on PyC substrates points to the creation of a more favorable surface for cell growth, and may correspond to stronger cellular adhesion.

EXAMPLES

Preparation of Samples

Mechanical heart valves of PyC were scored and broken into approximately 1 $cm^2$ pieces. Untreated polystyrene samples were obtained from Eagle Scientific, and used as received. All samples were sonicated in ethanol, and then rinsed in distilled water to remove surface contaminants. Following cleaning, samples were then allowed to dry completely in a dust free environment prior to experimentation.

PyC samples were used as substrates for both platelet and endothelial cell studies. Polystyrene samples were only used in cell studies as a negative control. Since it is a clear substrate that has been often used in previous experiments, the data generated from polystyrene samples allows for a more direct comparison.

Plasma Polymerization

The plasma glow discharge system used primarily consisted of a barrel reactor (see FIG. 2) with a diameter and depth of six inches (source: Extended Plasma Cleaner, Harrick Scientific, Ossining, N.Y.). A vacuum pump with an ultimate pressure of 1 mtorr and a pumping rate of 300 liters/min (Precision Scientific, P300, Winchester, Va.) was attached to the reaction chamber through a liquid nitrogen cold trap to prevent contamination of the reaction chamber. An oxygen gas inlet was connected to the opposite end of the reaction chamber (See FIG. 2). The pressure was monitored by a thermocouple vacuum gauge (Hastings Vacuum Gauge, DV-6).

Surface Analysis

Figure 3:
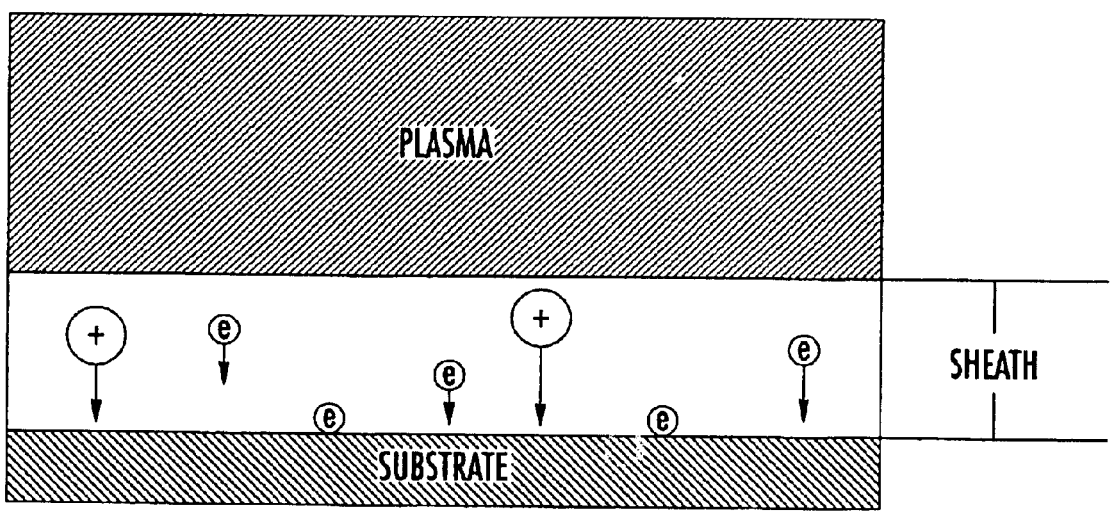
FIG. 3 shows plasma reactions causing radical formation on the substrate.
Figure 4:
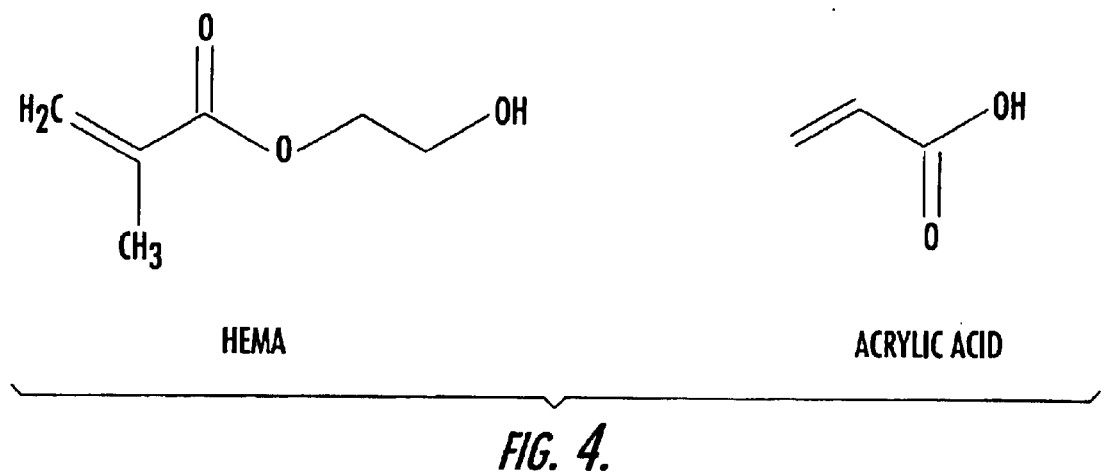
FIG. 4 illustrates one set of monomer structures that may be employed in coatings as applied in the invention.

Plasma deposition with oxygen gas was used to initiate a graft polymerization with HEMA and acrylic acid (See FIG. 3). Thereafter, untreated control samples, oxygen plasma deposited samples, along with HEMA and acrylic acid polymerized samples were each analyzed for differences in chemical composition and hydrophilicity. For the monomer structures employed in this particular Example, see FIG. 4. Numerous other monomers could be employed in the practice of the invention, and the invention is not limited to any particular monomer structure.

Electron spectroscopy for chemical analysis (ESCA) was used to determine the chemical composition of the samples. ESCA uses X-rays to excite the electrons of a material to a point at which they are released. These released electrons strike a detection pad, which measures the kinetic energy of the electrons. The kinetic energy can be used to calculate the binding energy of a particular electron. The binding energy of electrons is specific to the chemical bonds of which they originated, and can be used to distinguish different chemical bonds. With the exception of hydrogen and helium, all other elements can be detected.

A wide scan analysis was performed to determine all of the elements present, and high resolution scans were used to determine specific functionalities. Specifically, carbon atoms in different functional groups were identified with narrow scans of the C1s region at approximately 285 eV. The take off angle for all the scans was 90 degrees.

Contact angle measurements were taken using a goniometer for all treated and untreated samples to compare changes in hydrophilicity. By measuring the angle a drop of water makes with a given surface, a determination can be made as to whether a surface is hydrophilic or hydrophobic. The more spread out the drop is, the smaller the contact angle is, and the more hydrophilic the surface is. These measurements were taken with a drop size of 10 $\mu$L using the CAM 200 digital contact angle meter (KSV Instruments LTD).

The reaction chamber was evacuated to 10 mtorr to remove contaminants, particularly moisture. The chamber was then flooded with research grade oxygen gas (99.99%), and evacuated until a constant pressure of 150 mtorr was established, at which point a RF plasma of 30W was applied for ten minutes. Plasma treated PyC samples were then immersed into monomer solutions HEMA and acrylic acid for one hour to allow polymerization of the surface to react to its completion. Polystyrene samples were polymerized in the same manner, however only HEMA was used. The reaction was terminated, and excess monomer was removed by rinsing samples in distilled water. A plasma polymerized coating upon the support structure resulted.

Testing—Platelet Activation Studies

Platelet activation in response to plasma treated and untreated PyC was compared to reveal results. As expected, untreated PyC samples demonstrated severe platelet activation and aggregation. Also, untreated samples generated "thrombus-like" structures. Acrylic acid polymerized surfaces appeared to have less adherent platelets and thrombus-like structures than the control group. HEMA polymerized surfaces, on the other hand, exhibited a dramatic decrease in platelet adhesion and aggregation. See FIG. 5.

Figure 5:
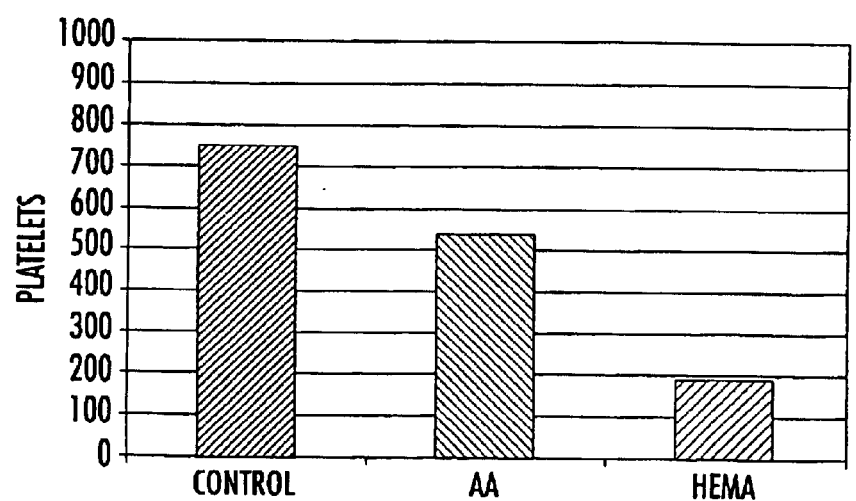
FIG. 5 shows data comparing the relative thrombogenicity of untreated pyrolitic carbon surfaces and plasma induced surface-modified pyrolytic carbon substrates.

A comparison of the average number of adherent platelet per given area was made in order to help quantify the relative thrombogenicity of each surface. The calculations revealed no significant difference between the untreated PyC samples and the acrylic acid polymerized surfaces, but a dramatic reduction was observed for HEMA polymerized surfaces. Platelet adhesion was reduced by over 75% when comparing the HEMA plasma polymerized coating to the untreated PyC. FIG. 5 shows these results in graphic form, with the level or degree of adherent platelets per square millimeter shown on the bar graph, where n=5, and alpha=0.05.

It is understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

What is claimed is:

1. An artificial biomaterial structure comprising:
   (a) a carbon-based support structure, wherein at least a portion of the carbon-based support structure defines a surface comprising pyrolytic carbon; and
   (b) an oxygen plasma induced polymerized coating directly adhered to the pyrolytic carbon surface, wherein said coating enhances endothelial cell growth and decreases platelet adhesion and aggregation on said biomaterial structure, wherein said coating is polymerized from solution onto the pyrolytic carbon surface, said surface being treated with a plasma consisting essentially of oxygen prior to the solution polymerization.

2. The artificial biomaterial structure of claim 1 wherein the artificial biomaterial structure is a bileaflet heart valve.

3. The artificial biomaterial structure claim 1 wherein the oxygen plasma induced polymerized coating comprises a film.

4. The artificial biomaterial structure claim 1 wherein the coating is formed from a monomer selected from the group consisting of: hydroxyls; carboxyls; sulfonates; and amines.

5. The artificial biomaterial structure claim 1 wherein the coating comprises a polymerized monomer of a methacrylate-containing species.

6. The artificial biomaterial structure claim 1 wherein the coating comprises a polymerized monomer of a styrene-containing species.

7. A vascular biomaterial comprising a tent, wherein the stent comprises a carbon-based support structure, wherein at least a portion of the carbon-based support structure defines a surface comprising pyrolytic carbon, the stent further comprising an oxygen plasma induced polymerized coating directly adhered to the pyrolytic carbon surface, wherein said coating is polymerized from solution onto the pyrolytic carbon surface, said surface being treated with a plasma consisting essentially of oxygen prior to the solution polymerization, wherein the coating enhances endothelial cell growth and decreases platelet adhesion and aggregation on said stent.

8. A vascular biomaterial comprising a vascular graft, the graft comprising a carbon-based support structure, wherein at least a portion of the carbon-based support structure defines a surface comprising pyrolytic carbon, the vascular biomaterial further comprising an oxygen plasma induced polymerized coating directly adhered to the pyrolytic carbon surface, wherein said coating is polymerized from solution onto the pyrolytic carbon surface, said surface being treated with a plasma consisting essentially of oxygen prior to the solution polymerization, wherein the coating enhances endothelial cell growth and decreases platelet activation and adhesion on the graft.

9. An artificial biomaterial structure comprising:
(a) a carbon-based support structure, wherein at least a portion of the carbon-based support structure defines a surface comprising pyrolytic carbon; and
(b) a coating directly adhered to the pyrolytic carbon surface, the coating comprising an oxygen plasma induced polymerized HEMA coating, wherein the HEMA coating increases the incidence of endothelialization and decreases the incidence of platelet adhesion and aggregation on the support structure, wherein said coating is polymerized from solution onto the pyrolytic carbon surface, said surface treated with a plasma consisting essentially of oxygen prior to the solution polymerization.

10. The artificial biomaterial structure of claim 9 in which the artificial biomaterial structure is an artificial heart valve, the heart valve comprising a suture ring positioned on an outer circumferential surface of the artificial heart valve.

11. A method of coating an artificial biomaterial structure with a polymer using plasma deposition techniques, comprising:

providing a monomer in solution,
providing an artificial biomaterial structure having a support structure,
treating a surface of the support structure with plasma consisting essentially of oxygen to generate a reactive surface, and
polymerizing the monomer on the reactive surface from the solution to form an oxygen plasma induced polymerized coating upon the support structure.

12. The method of claim 11 in which the artificial biomaterial structure comprises a bileaflet heart valve, a stent, or a vascular graft.

13. The method of claim 11 in which the monomer comprises HEMA.

14. The method of claim 11 wherein the monomer comprises acrylic acid.

15. The method of claim 11 wherein the monomer comprises olefinic monomers.

16. The method of claim 11 wherein the support structure comprises, pyrolytic carbon at the treated surface.

17. The method of claim 16 wherein the support structure consists of pyrolytic carbon.

18. The method of claim 11 wherein the oxygen plasma induced polymerized coating comprises a film.

19. The method of claim 18 wherein the film is capable of reducing platelet activation in vitro.

20. The method of claim 11 wherein the monomer comprises a methacrylate-containing species.

21. The method of claim 11 wherein the monomer comprises a styrene-containing species.

22. The artificial biomaterial structure of claim 1, wherein the artificial biomaterial structure is an artificial heart valve.

23. The vascular biomaterial of claim 7, wherein the coating comprises a polymerized monomer of a methacrylate-containing species.

24. The vascular biomaterial of claim 7, wherein the coating comprises a polymerized monomer of a styrene-containing species.

25. The vascular biomaterial of claim 7, wherein the coating comprises polymerized hydroxyethyl methacrylate.

26. The vascular biomaterial of claim 7, wherein the coating comprises polymerized acrylic acid.

27. The vascular biomaterial of claim 8, wherein the coating comprises a polymerized monomer of a methacrylate-containing species.

28. The vascular biomaterial of claim 8, wherein the coating comprises a polymerized monomer of a styrene-containing species.

29. The vascular biomaterial of claim 8, wherein the coating comprises polymerized hydroxyethyl methacrylate.

30. The vascular biomaterial of claim 8, wherein the coating comprises polymerized acrylic acid.

31. The artificial biomaterial structure of claim 9, wherein the artificial biomaterial structure is selected from the group consisting of a heart valve, a vascular graft and a stent.

32. The artificial biomaterial structure of claim 9, wherein the plasma polymerized coating consists essentially copolymerized HEMA.

33. The method of claim 11, wherein the monomer comprises functionality selected from the group consisting of hydroxyls, carboxyls, sulfonates, and amines.

* * * * *

UNITED STATES PATENT AND TRADEMARK OFFICE
CERTIFICATE OF CORRECTION

PATENT NO. : 6,837,903 B2
DATED : January 4, 2005
INVENTOR(S) : Naren R. Vyavahare and John Marigliano It is certified that error appears in the above-identified patent and that said Letters Patent is hereby corrected as shown below:

<u>Column 9,</u>
Lines 7, 10, 13 and 16, should read -- The artificial biomaterial structure of claim 1 --
Line 19, the word "tent" should be -- stent --

Signed and Sealed this

Twelfth Day of July, 2005

JON W. DUDAS
*Director of the United States Patent and Trademark Office*